(12) United States Patent
Cullen

(10) Patent No.: US 7,972,293 B2
(45) Date of Patent: Jul. 5, 2011

(54) NASAL FLUID RELIEF PLUG

(76) Inventor: Michelle Cullen, Northbrook, IL (US)

( * ) Notice: Subject to any disclaimer, the term of this patent is extended or adjusted under 35 U.S.C. 154(b) by 474 days.

(21) Appl. No.: 12/151,787

(22) Filed: May 10, 2008

(65) Prior Publication Data
US 2009/0281622 A1    Nov. 12, 2009

(51) Int. Cl.
*A61F 13/20* (2006.01)
(52) U.S. Cl. ........... 604/11; 604/8; 604/907; 28/118
(58) Field of Classification Search ........ 604/11, 604/18; 128/206.11; 28/118
See application file for complete search history.

(56) References Cited

U.S. PATENT DOCUMENTS

| 1,051,850 | A | | 1/1913 | Sandmark |
| 2,490,168 | A | | 12/1949 | Strauss |
| 4,457,756 | A | | 7/1984 | Kern |
| 4,573,461 | A | * | 3/1986 | Lake ............ 128/201.18 |
| 4,646,739 | A | | 3/1987 | Doyle |
| 4,883,465 | A | | 11/1989 | Brennan |
| 4,887,597 | A | * | 12/1989 | Holland ............ 128/206.11 |
| 5,383,891 | A | | 1/1995 | Walker |
| 7,294,138 | B2 | | 11/2007 | Shippert |

FOREIGN PATENT DOCUMENTS

| CN | 201085740 Y | * | 7/2008 |
| DE | 2141252 B | * | 4/1977 |

* cited by examiner

*Primary Examiner* — Jacqueline F Stephens
(74) *Attorney, Agent, or Firm* — Patzik, Frank & Samotny Ltd.

(57) ABSTRACT

A nasal plug for preventing excessive fluid discharge from a nasal passage includes a plug element fabricated from an absorbent material. The plug element has a size and configuration adapted and constructed to fit into a human nasal passage. A shaft portion extends from the plug element. The shaft portion is formed as an extension of the plug element and is fabricated from the same material as the plug element. A flexible sheathing is provided on the shaft portion.

12 Claims, 3 Drawing Sheets

NASAL FLUID RELIEF PLUG

CROSS-REFERENCE TO RELATED APPLICATION

BACKGROUND OF THE INVENTION

Although a great number of human maladies can include nasal discharge as a symptom, perhaps the most ubiquitous is viral rhinitis, more familiarly known as the "common cold". A cold is a viral infection, characterized by nasal congestion, a clear, runny nose, sneezing, scratchy throat and general malaise. The name "common cold" came into use in the 16th century, due to the similarity between its symptoms and those of exposure to cold weather. The causes and treatment of cold symptoms has been the subject of much inquiry through the centuries. In the 1700's, Benjamin Franklin applied his considerable intellect and energy to the causes and prevention of the common cold. After several years of research he concluded: "People often catch cold from one another when shut up together in small close rooms, coaches, etc. and when sitting near and conversing so as to breathe in each other's transpiration." Although viruses had not yet been discovered, Franklin hypothesized that the common cold was passed between people through the air. He recommended exercise, bathing, and moderation in food and drink consumption to avoid the common cold. Franklin's theory on the transmission of the cold was confirmed some 150 years later.

Perhaps the most annoying and troublesome cold symptom is excessive nasal discharge. Various devices and methods have been developed to assist in the management of nasal discharge, whether nasal mucus from a cold or allergies, or other fluids from other causes, such as blood from an injury. Many of these devices and methods are represented in the patent literature. For example, U.S. Pat. No. 1,051,850 to Sandmark is directed to a surgical appliance which may be used in stopping the bleeding of membranes in nasal passages.

U.S. Pat. No. 2,490,168 to Strauss describes a sinus medicine applicator.

U.S. Pat. No. 4,457,756 to Kern deals with a device for treatment of nose bleed. The invention in a preferred embodiment takes the form of a bifurcated clip having opposed legs connected by a bight portion to gently urge the distal ends of the legs toward each other. The distal end of each leg is provided with an absorbent pad substantially saturated with a vasoconstrictive agent, the ends of the clip and thus the medicated pads disposed on the clip ends being slipped into the nose in the event of nose bleed. The pads contact those portions of the nasal mucosa lying on the septum immediately inside of the nostrils, common nose Weed typically occurring from these portions of the nasal mucosa. A stop element disposed on at least one of the legs prevents insertion of the clip ends beyond a safe distance into the nasal cavity. The action of the vasoconstrictive agent on the mucosa as well as the gentle pressure exerted by the clip itself acts to control bleeding. The pressure exerted by the clip can further be augmented by finger pressure on external portions of the clip or on the external surfaces of the tip of the nose.

U.S. Pat. No. 4,646,756 to Doyle shows a nasal hemostat adapted for insertion into a nasal cavity by individuals not trained in medical or nursing arts. The hemostat is composed of contracted material adapted to expand into a porous tampon upon contact with a fluid. The contracted tampon is in the form of an elongated rectangle. Upon expansion, the tampon assumes the shape of a small, right-angled triangle adjacent to a truncated isosceles triangle, connected by a common top, having a linear top wall and two parallel side walls. Upon expansion, the tampon will apply hemostatic pressure to substantially all parts of the most important area of the nasal cavity in regards to hemorrhage. Furthermore, the shape of the tampon is such that there should be essentially no waste from the raw material used in the manufacture of said tampon, thereby greatly decreasing manufacturing costs and allowing the tampon to be more readily available to the nonmedical public.

U.S. Pat. No. 4,883,465 to Brennan is concerned with a nasal tampon adapted for use during a nasal surgery. The tampon comprises an expansible low pressure sealing cuff, an inflation conduit, a drainage conduit, and an absorptive member. The tampon is designed to control nasal hemorrhaging without exerting direct pressure on the bleeding area. The expansible cuff conforms to the inner walls of the choanae and forming a seal therebetween so as to occlude the passageway and thereby prevent the flow of Blood and other fluids down the patient's throat.

U.S. Pat. No. 5,383,891 to Walker describes a hemostatic tampon kit including an oval-shaped tampon adopted for easy insertion into the nasal cavity by a layman. The tampon is composed of a compressed synthetic sponge adapted to expand upon contact with an aqueous fluid, the tampon includes a string attached thereto for anchoring to a nasal bandage placed over the nostrils of the user. The sponge includes an absorbent drip pad and an attachment element on the bandage for engaging and holding the tampon string. A scalable container of liquid vasoconstrictive medication may be provided for wetting and expanding the tampon and a container of anti-bacterial ointment for lubricating the tampon during insertion.

U.S. Pat. No. 7,294,138 to Shippert is directed to a medical device and method for treating nose bleeds. The device includes packing material interconnected to a flange member. The packing material is insertable into a nasal cavity, for absorbing blood and other body fluids. The flange member prevents the packing material from being inhaled or otherwise moving in an anterior direction. In addition, the flange member obscures a view of the interior of the user's nasal cavity, and therefore of blood within the cavity, or of blood that has been absorbed by the packing member.

Although the arrangements described in these patents provide certain advantages, they present certain deficiencies as well. For example, they fail to provide a mechanism for relieving the uncomfortable discharge from one nostril while a patient is in a reclining position. Further, many of these devices are relatively complicated and uncomfortable to implement. It can thus be seen that the need exists for a simple, efficient, and easily usable arrangement for preventing nasal discharge for a cold sufferer.

SUMMARY OF THE INVENTION

According to one aspect of the invention, a nasal plug for preventing excessive fluid discharge from a nasal passage includes a plug element fabricated from an absorbent material. The plug element has a size and configuration adapted and constructed to fit into a human nasal passage. A shaft portion extends from the plug element. The shaft portion is formed as an extension of the plug element and is fabricated from the same material as the plug element. A flexible sheathing is provided on the shaft portion.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWING

Embodiments of the invention are illustrated by way of example, and not by way of limitation, in the figures of the accompanying drawings and in which like reference numerals refer to similar elements and in which.

DETAILED DESCRIPTION OF THE INVENTION

Figure 1:
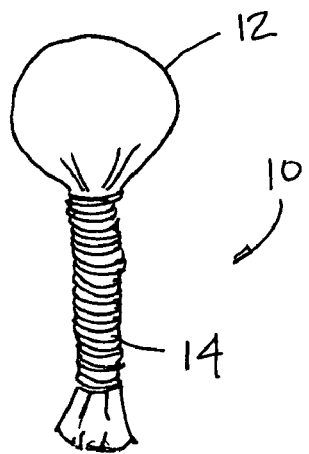
FIG. 1 illustrates a perspective view of embodiment of a nasal plug in accordance with the principles of the present invention.

In the following description, specific details are set forth in order to provide a thorough understanding of the invention. However, it will be apparent that the invention may be practiced without these specific details. Without departing from the generality of the invention disclosed herein and without limiting the scope of the invention, the discussion that follows, will refer to the invention as depicted in the drawing.

Figure 2:
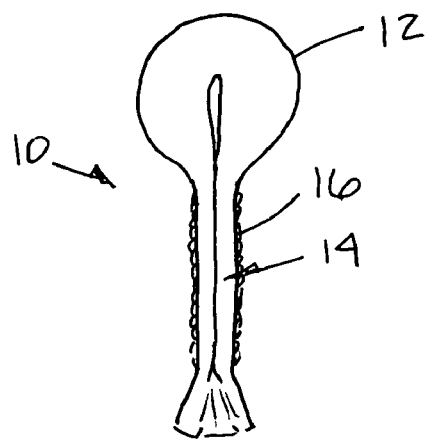
FIG. 2 illustrates a sectional view of the nasal plug shown in FIG. 1.

According to one embodiment, a nasal plug 10 in accordance with the principles of the present invention is illustrated in FIGS. 1 and 2. The nasal plug 10 includes a plug element 12 fabricated from an absorbent material. Although any suitable absorbent material may be employed, it is contemplated that particular advantages can be achieved by using absorbent materials commonly used in the manufacture of tampons, feminine products, and the like. Examples of such materials include, but are not limited to, cotton, and blends of cotton and rayon.

A shaft portion 14 extends from the plug element 12. The shaft portion 14 is formed as an extension of the plug element 12, and is fabricated from the same material as the plug element 12.

A flexible sheathing 16 is provided on the shaft portion 14. The sheathing 14 is fabricated from a material that will provide a moisture barrier to liquid absorbed by the plug element 12 and, to a lesser degree, by the shaft portion 14. The sheathing 16 is advantageously flexible to enhance the safety and comfort of the user of the nasal plug 10. As shown in FIGS. 1 and 2, the sheathing 16 is formed by winding a textile material, such as cotton thread, around a part of the length of the shaft portion 14.

Figure 3:
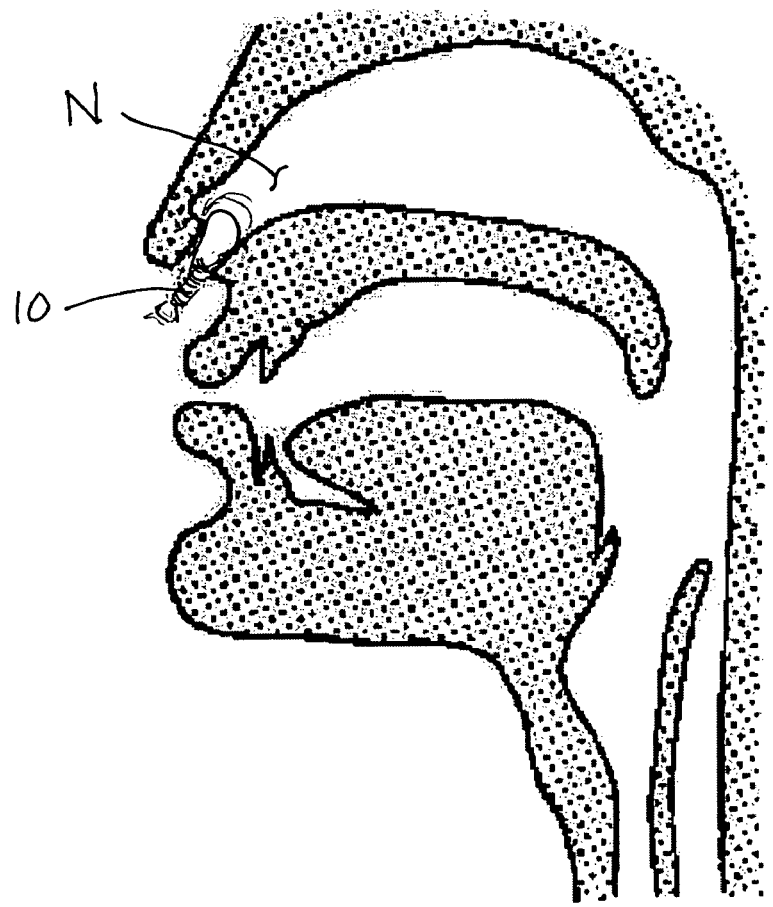
FIG. 3 illustrates a nasal plug in accordance with the principles of the present invention in place in a nasal passage.

As shown in FIG. 3, the plug element 12 of the nasal plug 10 is formed to have a size and configuration that is adapted and constructed to fit into a human nasal passage N. In practice, the plug 12 can be provided in various sizes to fit various individuals, e.g., adults or children. When inserted as illustrated, the nasal plug 10 inhibits the flow of nasal mucus from the nasal passage N. This is of particular utility when a user is sleeping, as the nasal plug can be inserted into the "lower" nasal passage of the user (e.g., the left nostril of a person sleeping with the left side of his or her head on the sleeping surface). In a person sleeping in such a position unaided by the nasal plug 10 of the present invention, the person is usually able to breathe freely through the right or "upper" nostril, while nasal discharge flows through the lower nostril. The resultant discharge typically interrupts the sleep of the person, preventing sufficient rest and likely prolonging the underlying malady. With the nasal plug 10 of the present invention in place, the person is usually able to breathe freely through the right or "upper" nostril, while nasal discharge through the lower nostril is prevented. It is also contemplated that the plug element 12 of the nasal plug 10 can be coated or impregnated with a medicament to ease the symptoms or shorten the duration of the underlying malady. Such medicaments can include prescription medicines, homeopathic treatments and the like. Further, the nasal plug 10 can be provided with colors or to enhance the therapeutic and/or marketing aspects of the product.

Figure 4:
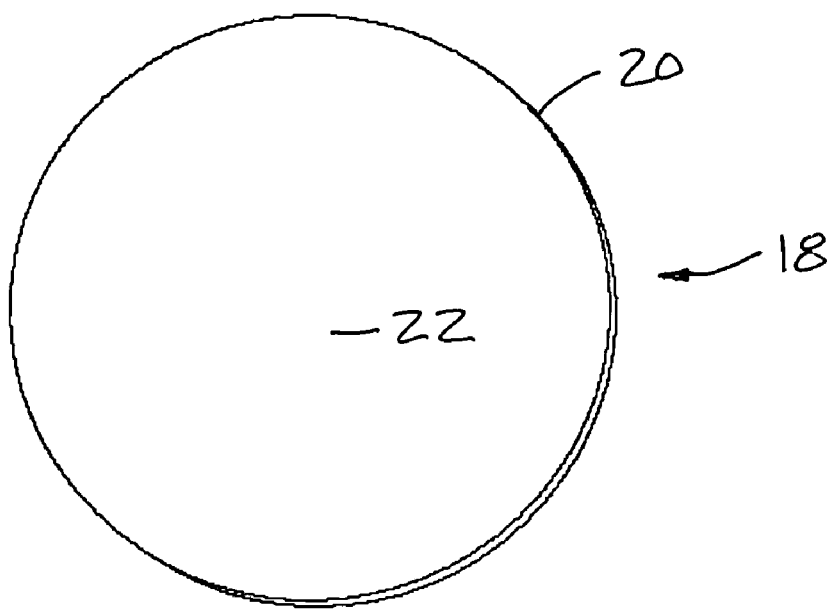
FIG. 4 illustrates a circular blank of absorbent material before fabrication of a nasal plug.
Figure 5:
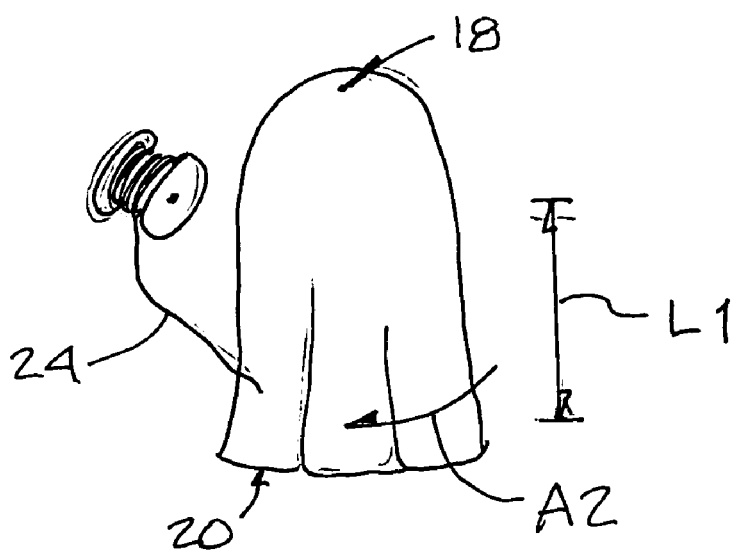
FIG. 5 illustrates a circular blank of absorbent material gathered peripherally.

An exemplary method of forming a nasal plug for the prevention of excessive nasal discharge is shown in FIGS. 4 and 5. FIG. 4 illustrates a circular blank 18 of absorbent material having an outer edge 20 and a center 22. In FIG. 5, the circular blank 18 is gathered peripherally, so that the edge 20 forms a bottom of an intermediate stage of formation. Next, the gathered blank of absorbent material 18 is constricted along part of its length L1 to form a shaft portion and a plug element as shown in FIG. 1. In this example, the constriction is accomplished by winding a length of thread 24 around the length L1 in the direction of the arrow A1, thus forming a sheath. The materials for the circular blank 18 and the thread 24 are the same as described with respect to FIGS. 1 and 2.

Figure 6:
FIG. 6 illustrates an elongate strip of absorbent material before fabrication of a nasal plug.
Figure 7:
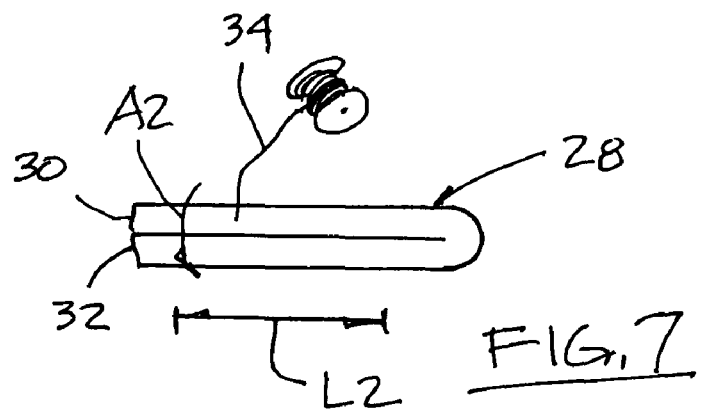
FIG. 7 illustrates a strip of absorbent material doubled on itself.

Another exemplary method of forming a nasal plug for the prevention of excessive nasal discharge is shown in FIGS. 6 and 7. FIG. 6 illustrates an elongate strip 28 of absorbent material having first and second ends 30, 32. In FIG. 7, the elongate strip 28 is folded in half, so that the first and second ends 30, 32 have been brought together. Next, the folded absorbent material 28 is constricted along part of its length L2 to form a shaft portion and a plug element as shown in FIG. 1. In this example, the constriction is accomplished by winding a length of thread 34 around the part L2 in the direction of the arrow A2, thus forming a sheath. The materials for the absorbent strip 28 and the thread 34 are the same as described with respect to FIGS. 1 and 2.

Figure 8:
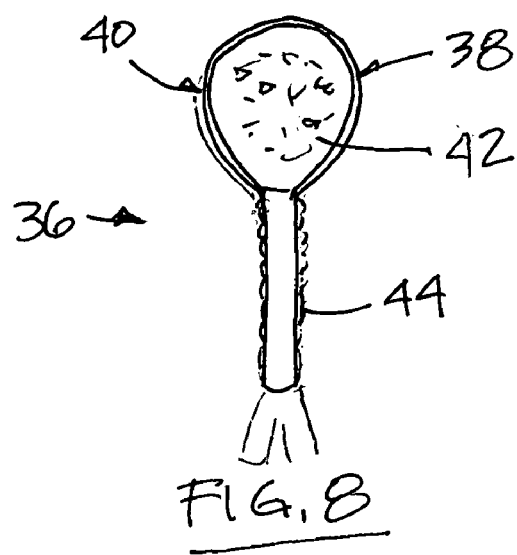
FIG. 8 illustrates a sectional view of another embodiment of a nasal plug in accordance with the principles of the present invention.

Another embodiment of a nasal plug 36 in accordance with the principles of the present invention is shown in FIG. 8. The nasal plug 36 includes a plug element 38 having an outer layer 40 and an inner core 42. The outer layer 40 is fabricated from a wicking material, such as woven cotton fabric, designed to draw fluid from the nasal membrane of the user. The core 42 is fabricated from a less absorbent material (such as batting of the type used in diapers) designed to more slowly absorb and retain the flow of nasal fluid. A shaft portion 44 is provided as previously described.

While this invention has been described in connection with the best mode presently contemplated by the inventor for carrying out his invention, the preferred embodiments described and shown are for purposes of illustration only, and are not to be construed as constituting any limitations of the invention. Modifications will be obvious to those skilled in the art, and all modifications that do not depart from the spirit of the invention are intended to be included within the scope of the appended claims. Those skilled in the art will appreciate that the conception upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The invention resides not in any one of these features per se, but rather in the particular combinations of some or all of them herein disclosed and claimed and it is distinguished from the prior art in these particular combinations of some or all of its structures for the functions specified.

With respect to the above description then, it is to be realized that the optimum dimensional relationships for the parts of the invention, including variations in size, materials, shape, form, function and manner of operation, assembly and use, and all equivalent relationships to those illustrated in the drawings and described in the specification, that would be deemed readily apparent and obvious to one skilled in the art, are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim as my invention:

1. A method of forming a nasal plug for the prevention of excessive nasal discharge, the method comprising the following steps:
    providing an elongate strip of absorbent material having first and second ends;
    folding the elongate strip in half so that the first and second ends are brought together; and
    constricting a portion of the folded absorbent material along its length to form a shaft portion and a plug element.

2. A method in accordance with claim 1, wherein the step of providing an elongate strip of absorbent material further comprises providing a strip of textile material.

3. A method in accordance with claim 2, wherein the step of providing an elongate strip of absorbent material further comprises providing a strip of cotton material.

4. A method in accordance with claim 2, wherein the step of providing an elongate strip of absorbent material further comprises providing a strip of material fabricated from a blend of cotton and rayon.

5. A method in accordance with claim 1, wherein the step of constricting a portion of the folded absorbent material comprises forming a sheathing around a portion of the folded absorbent material.

6. A method in accordance with claim 5, wherein the step of forming a sheathing around a portion of the folded absorbent material comprises winding a length of thread around a portion of the folded absorbent material.

7. A method of forming a nasal plug for the prevention of excessive nasal discharge, the method comprising the following steps:
    providing a circular blank of absorbent material having an outer edge;
    gathering the circular blank peripherally so that the outer edge forms a bottom; and
    constricting a portion of gathered circular blank material along its length to form a shaft portion and a plug element.

8. A method in accordance with claim 7, wherein the step of providing a circular blank of absorbent material further comprises providing a circular blank of textile material.

9. A method in accordance with claim 8, wherein the step of providing a circular blank of absorbent material further comprises providing a circular blank of cotton material.

10. A method in accordance with claim 8, wherein the step of providing a circular blank of absorbent material further comprises providing a circular blank of material fabricated from a blend of cotton and rayon.

11. A method in accordance with claim 7, wherein the step of constricting a portion of the gathered absorbent material comprises forming a sheathing around a portion of the gathered absorbent material.

12. A method in accordance with claim 11, wherein the step of forming a sheathing around a portion of the gathered absorbent material comprises winding a length of thread around a portion of the gathered absorbent material.

* * * * *